United States Patent
Ibaraki et al.

(10) Patent No.: US 6,773,925 B2
(45) Date of Patent: Aug. 10, 2004

(54) DETECTOR AGENT FOR HALOGEN COMPOUNDS AND METHOD FOR DETECTING HALOGEN COMPOUNDS

(75) Inventors: Yoshihiro Ibaraki, Tokyo (JP); Hideji Kawanaka, Tokyo (JP); Hidekazu Ina, Tokyo (JP); Shinichi Ando, Tokyo (JP)

(73) Assignees: L'Air Liquide Societe Anonyme a Directoire et Conseil de Surveillance Pour l'Etude et l'Exploitation des Procedes Georges Claude, Paris (FR); Air Liquide Electronics Systems, Paris (FR)

( * ) Notice: Subject to any disclaimer, the term of this patent is extended or adjusted under 35 U.S.C. 154(b) by 316 days.

(21) Appl. No.: 09/767,704

(22) Filed: Jan. 24, 2001

(65) Prior Publication Data

US 2001/0012635 A1 Aug. 9, 2001

(30) Foreign Application Priority Data

Feb. 2, 2000 (JP) ........................................ 2000-025331

(51) Int. Cl.⁷ ............................................. G01N 33/00
(52) U.S. Cl. .................... 436/124; 436/101; 436/160; 436/164; 422/86; 422/87; 422/88; 422/85; 423/240; 423/241
(58) Field of Search ................................. 436/124, 101, 436/160, 164; 422/86, 87, 88, 85; 423/240, 241

(56) References Cited

U.S. PATENT DOCUMENTS

| | | | | |
|---|---|---|---|---|
| 4,333,893 A | * | 6/1982 | Clyde | 261/94 |
| 6,060,034 A | * | 5/2000 | Tsukamoto | 423/240 S |
| 6,287,518 B1 | * | 9/2001 | Ignacio et al. | 422/86 |

* cited by examiner

*Primary Examiner*—Jill Warden
*Assistant Examiner*—Sam P. Siefke
(74) *Attorney, Agent, or Firm*—Burns, Doane, Swecker & Mathis, L.L.P

(57) ABSTRACT

There are provided a detector agent which is effectively discolored at a lower concentration for various halogen compounds and a method for detecting halogen compounds by use of said detector agent.

Figure 1:
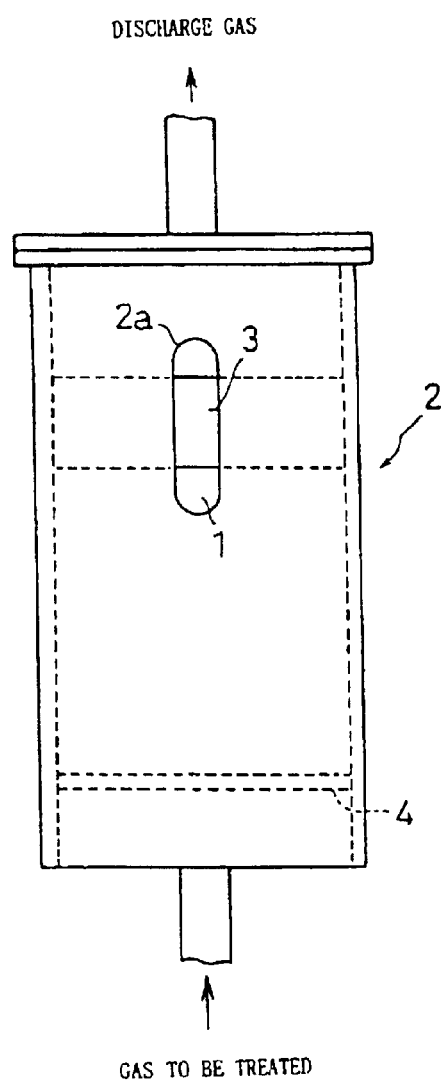

A detector agent for halogen compounds, which contains curcumin or Bromocresol Green as a discoloring component, and said discoloring component is preferably supported on granular activated alumina.

6 Claims, 1 Drawing Sheet

DETECTOR AGENT FOR HALOGEN COMPOUNDS AND METHOD FOR DETECTING HALOGEN COMPOUNDS

BACKGROUND OF THE INVENTION

1. Field of the Invention

The present invention relates to a detector agent for halogen compounds, which contains curcumin or Bromocresol Green as a discoloring component, and a method for detecting halogen compounds by use of said detector agent, and the present invention is usual to judge the leakage of halogen compounds which are used in a semiconductor-manufacturing plant or the like or the break-though of a solid treatment agent for removal of harmful substances.

2. Description of the Related Art

Gases containing halogen compounds such as F2, Cl2, FCl3, HF, BrF5 and SiCl4 are useful in many applications, for instance, in a field of chemical industries including a semiconductor-manufacturing plant so as to utilize a higher reactivity of halogen atoms. In a case where they are used, various halogen compounds are produced as their reaction products. These halogen compounds possess in many cases a higher reactivity, in which their danger and toxicity are intensive. Accordingly, it is not permitted to release gases containing these halogen compounds as they are, and it is desired to release them to the atmosphere after they are made harmless by a harmful substances removal apparatus.

As such a harmful substances removal apparatus as mentioned above, there have been known apparatuses for removing or decomposing halogen compounds through a wet treatment such as an alkali scrubber or a dry treatment using a solid treatment agent such as a decomposition catalyst, solid reaction agent or adsorbent. In a case where a solid treatment agent is used, it is necessary to detect halogen compounds on the downstream side thereof so that the deterioration of the solid treatment agent is judged because it has a life time (a break-though time) determined by its catalyst poisoning, reactive deterioration or adsorptive saturation.

As for a method for detecting halogen compounds, a method of using a detector agent which is discolored due to the presence of halogen compounds is simple. There has been known, for example, a detector agent containing a molybdate as a discoloring component for dichlorosilane.

For various halogen compounds which are used in a semiconductor-manufacturing plant or the like, however, there has not been known till now a detector agent which is effectively discolored at a lower concentration. In addition, curcumin or Bromocresol Green has been known only as a discoloring component for the detection of boron or the indication of pH.

It is therefore an object of the present invention to provide a detector agent which is effectively discolored at a lower concentration for various halogen compounds and a method for detecting halogen compounds by use of said detector agent.

SUMMARY OF THE INVENTION

In order to achieve the aforementioned purpose, the inventors have studied hard the usability of various kinds of coloring compounds, have found a fact that the aforementioned purpose can be achieved by using curcumin or Bromocresol Green as a discoloring component, and have completed the present invention.

Namely, the detector agent according to the present invention is a detector agent for halogen compounds, which contains curcumin as a discoloring component, or a detector agent for halogen compounds, which contains Bromocresol Green as a discoloring component.

In the above-mentioned detector agent, said discoloring component is preferably supported on granular activated alumina.

On the other hand, the detecting method according to the present invention is a method for detecting halogen compounds, which comprises bringing anyone of said detector agents into contact with a gas to be detected that may contain halogen compounds, as said detector agent is disposed on a position where it can be visually observed from the outside.

Furthermore, the detecting method according to the present invention is a method for detecting halogen compounds, which comprises visually observing from the outside anyone of said detector agents disposed on the upper layer of a solid treatment agent for removing or decomposing halogen compounds, as a gas to be treated is caused for treatment to flow from the bottom side of a container filled with said solid treatment agent, whereby halogen compounds are detected to judge the deterioration of said solid treatment agent.

BRIEF DESCRIPTION OF THE FIGURE OF THE DRAWING

The FIGURE of the Drawing is a front view showing one example of the apparatus used in the detecting method according to the present invention.

The Reference Numerals refer to 1—solid treatment agent, 2—container, 2a—inspection hole, 3—detector agent.

DETAILED DESCRIPTION OF THE PREFERRED EMBODIMENTS

Since curcumin or Bromocresol Green is contained as a discoloring component, according to the detector agent of the present invention, there can be provided a detector agent which is effectively discolored at a lower concentration for various halogen compounds, as the results of Examples exhibit.

In a case where said discoloring component is supported on granular activated alumina, the detecting sensitivity thereof is enhanced because the effective contact area of the discoloring component is increased and it becomes easy to visually observe the change in color tone. Furthermore, the fluidity of a gas to be detected becomes well.

Since such a detector agent as mentioned above is brought into contact with a gas to be detected that may contain halogen compounds, as said detector agent is disposed on a position where it can be visually observed from the outside, according to a detecting method of the present invention, on the other hand, an effective detection at a lower concentration can be performed for various halogen compounds.

Since various halogen compounds contained in a gas left after treatment can be effectively detected at a lower concentration by such a simple method that a detector agent is disposed on the upper layer of a solid treatment agent, as mentioned above, according to another detecting method of the present invention, the deterioration of said solid treatment agent can be securely judged.

EMBODIMENTS OF THE INVENTION

Embodiments of the present invention will be described below in an order of the detector agent for halogen compounds and the method for detecting halogen compounds.

(Detector Agent for Halogen Compounds)

As halogen compounds which can be detected in the present invention, there are exemplified $SiH_2Cl_2$, HF, $F_2$, HBr, $Cl_2$, $ClF_3$, $TiCl_4$, $BCl_3$, HL and etc., in a case where curcumin is contained as a discoloring component. And further there are exemplified $SiH_2Cl_2$, HF, $Cl_2$, $BCl_3$, $SiHCl_3$, $BF_3$, $SiF_4$, $SiCl_4$, $WF_6$ and etc., in a case where Bromocresol Green is contained as a discoloring component.

Curcumin which is one kind of diketones has a chemical formula of $C_{21}H_{20}O_6$ and is orange crystal having a melting point of 183° C., and it is used as a discoloring component for the detection of boron or the indication of pH. Curcumin exhibits a yellowish orange appearance when it is supported in a proper amount on a carrier.

Bromocresol Green has a chemical formula of $C_{21}H_{14}Br_4O_5S$ and is colorless crystal having a melting point of 217° C., and it is used as a discoloring component for the indication of pH. Bromocresol Green exhibits a blue appearance when it is supported in a proper amount on a carrier such as activated alumine.

It is preferable, for using both these discoloring components as a detector agent, to support or deposit them on a granular material or the like, and more preferable to use them as they are supported on a granular porous carrier. Although various materials such as alumina, silica gel and diatomaceous earth can be used as the carrier, white materials are preferable and granular activated alumina is preferred because of the above-mentioned reasons. In addition, the grain size of such granular carriers is preferably 2~5 mm.

As for a method of supporting said discoloring component on a carrier, there are used any methods. Namely, such discoloring component can be supported on a carrier, for instance, by a conventional known method which comprises dissolving curcumin or Bromocresol Green in a suitable solvent such as alcohol, immersing a carrier in the resulting mixture, and then drying the carrier to remove the solvent. In a case where a discoloring component is used as it is supported on a carrier, the supporting quantity is preferably 0.001~0.1 wt %. If the supporting quantity becomes too larger, the discoloring becomes difficult to judge, and if the supporting quantity becomes contrarily too smaller, the discoloring is not almost seen even when the discoloring component is contacted with halogen compounds.

Furthermore, a discoloring component may be supported or deposited on fibers, a fiber cloth or a porous membrane. In this case, the supporting or deposition of a discoloring component will be satisfactorily carried out by impregnating or coating a solution of a discoloring component in or on these carriers and then drying them to remove a solvent, similarly to the case of the above-mentioned carriers. In order to be prevented from being discolored, in addition, the detector agent of the present invention is preferably preserved as it is protected from moisture and direct sunlight, for instance, by being put in a vinyl bag.

Method of Detecting Halogen Compounds

The detecting method according to the present invention comprises bringing a detector agent of the present invention into contact with a gas to be detected that may contain halogen compounds, as the detector agent is disposed on a position where it can be visually observed from the outside. Concretely, this detecting method will be satisfactorily carried out by charging said detector agent in a drum (column) which is transparent at least in part, as in a case of such kind of detector agent of the prior art, and causing a gas to be detected, for example a discharge gas which has been subjected to a harmful substances removal treatment, to flow at a proper speed through said column.

While the temperature condition on contact may be normal temperature at that time, the detector agent is usable also at an elevated temperature (for example, 60~80° C.) in the harmful substances treatment. Since the discoloring is caused occasionally when moisture is contained in a gas to be detected, in addition, the gas to be detected may be previously treated by a drying agent or the like. Further, the column is preferably disposed by excepting a position where sunlight is directly irradiated thereto.

A preferred embodiment of to the present invention comprises, as shown in the FIGURE of the drawings, visually observing from the outside a detector agent 3 disposed on the upper layer of a solid treatment agent 1 for removing or decomposing halogen compounds, as a gas to be treated is caused for treatment to flow from the bottom side of a container 2 filled with said solid treatment agent 1, whereby halogen compounds are detected to judge the deterioration of said solid treatment agent 1.

In the inside of said container 2 is provided a support plate 4 possessing a dispersing function for the gas to be treated and a supporting function for the solid treatment agent 1, and on the peripheral wall of the container 2 is provided an inspection hole 2a, through which the detector agent 3 can be visually observed from the outside. And further, a heating means (not shown) for heating the solid treatment agent 1 to a temperature suitable for the removal or decomposition of halogen compounds is provided round the periphery of the container 2 or in the inside thereof, as necessary.

As the solid treatment agent 1, there can be used anyone of known decomposition catalysts, solid reaction agents, adsorbents and the likes which remove or decompose halogen compounds. The solid treatment agent 1 is properly heated to a temperature depending on its kind by the heating means, and the quantity (the charging height) of the solid treatment agent 1 and the feed flow rate of a gas to be treated are properly set.

The charging height of the detector agent 3 is preferably more than 50 mm, and the discharge quantity of halogen compounds can be estimated in a some extent in accordance with the discoloring speed of the detector agent 3. Accordingly, the solid treatment agent 1 can be exchanged at a suitable point of time, by previously making the exchanging point of time due to the deterioration of the solid treatment agent 1 to correspond to the discoloring speed of the detector agent 3 depending on the kind or the like of the solid treatment agent 1. Moreover, the concentration of halogen compounds in a discharge gas can be maintained at a concentration lower than TLV value, by predetermining the height of the discoloring as a reference of the odor allowable concentration (TLV value) based on ACGIH in 1988.

EXAMPLES

In the next place, examples which concretely exhibit the composition and effects of the present invention will be described.

Example 1

0.5 g of powdery curcumin was mixed and stirred in 2.5L of ethanol so as to be dissolved therein and 5 Kg of activated alumina with a diameter of about 4 mm were further mixed therein, and the resulting mixture was continuously stirred until the activated alumina was homogenously colored with an orange color. This colored activated alumina was separated from the liquid and dried at about 60° C. in a drier so that ethanol remaining therein was sufficiently removed.

Thus, a yellowish orange detector agent containing curcumin as a discoloring component (at the supporting quantity of 0.01 wt %) was prepared.

This detector agent was charged to a height of about 50 mm in a transparent glass tube (with an inner diameter of 50 mm). Gases (at normal temperature) containing halogen compounds given in Table 1 at different concentrations were fed thereto in turn at 1 L/min. The discoloring was visually observed to examine the color left after the discoloring and the minimum concentration, at that the discoloring was caused. And the results are given in Table 1.

TABLE 1

| Halogen Compounds | Coloration | Detecting Sensitivity (ppm) |
| --- | --- | --- |
| SiH2Cl2 | Thick green | 5 |
| HF | Yellow | 3 |
| F2 | White | 1 |
| HBr | White | 3 |
| Cl2 | White | 0.5 |

Example 2

Bromocresol Green 1 g of powdery Bromocresol Green was mixed and stirred in 2.5L of ethanol so as to be dissolved therein and 5 Kg of activated alumina with a diameter of about 4 mm were further mixed therein, and the resulting mixture was continuously stirred until the activated alumina was homogenously colored with a blue color. This colored activated alumina was separated from the liquid and dried at normal temperature so that ethanol remaining therein was removed. Thus, a blue detector agent containing Bromocresol Green as a discoloring component (at the supporting quantity of 0.02 wt %) was prepared.

This detector agent was charged to a height of about 50 mm in a transparent glass tube (with an inner diameter of 50 mm). Gases (at normal temperature) containing halogen compounds given in Table 2 at different concentrations were fed thereto in turn at 1 L/min. The discoloring was visually observed to examine the color left after the discoloring and the minimum concentration, at that the discoloring was caused. And the results are given in Table 2.

TABLE 2

| Halogen Compounds | Coloration | Detecting Sensitivity (ppm) |
| --- | --- | --- |
| SiH2Cl2 | White | 5 |
| HF | White | 3 |
| Cl2 | White | 0.5 |
| BCl3 | White | 5 |
| SiHCl3 | White | 5 |
| BF3 | White | 1 |

Example 3

A solid treatment agent was charged to a height of 300 mm in such a harmful substances removal column as shown in FIG. 1, which had an inner diameter of 150 mm, and the detector agent obtained in Example 1 was charged to a height of about 50 mm on the upper layer thereof. A gas to be treated, which contained 2,000 ppm of F2 in nitrogen gas, was caused to flow at 20 L/min. from the lower portion of the harmful substances removal column, as the detector agent was visually observed from the outside, whereby a treatment of reacting and solidifying F2 at normal temperature was performed.

After the elapse of about 90 hours, the detector agent began to discolor to white color from the lower portion of its charged layer, and at a point of time when it was discolored up to a position of 80%, the concentration of F2 in a discharge gas was measured by a F2 detector based on the diaphragm electrode method. As a result, the concentration of F2 was 0~0.5 ppm and this was a value lower than TLV value. At this point of time, it could be judged that the capability of the solid treatment agent was almost saturated.

What is claimed is:

1. A method for detecting at least one halogen compound which comprises bringing a detector agent for detecting a halogen compound, which comprises curcumin as a discoloring component, into contact with a gas to be detected that may contain a halogen compound, as said detector agent is disposed in a position where it can be visually observed, and wherein the halogen compound to be detected is selected from the group consisting of $SiH_2Cl_2$, HF, $F_2$, HBr, $ClF_3$, $TiCl_4$, $BCl_3$, HI and mixtures thereof.

2. A method for detecting at least one compound, which comprises visually observing a detector agent for detecting a halogen compound, which comprises curcumin as a discoloring component, wherein the detector agent is disposed on an upper layer of a solid treatment agent for removing or decomposing a halogen compound, as a gas to be treated is caused to flow from a bottom side of a container containing said solid treatment agent, whereby a halogen compound is detected to judge the deterioration of said solid treatment agent, and wherein the halogen compound to be detected is selected from the group consisting of $SiH_2Cl_2$, HF, $F_2$, HBr, $ClF_3$, $TiCl_4$, $BCl_3$, HI and mixtures thereof.

3. A method for detecting at least one halogen compound, which comprises bringing a detector agent for detecting a halogen compound, which comprises curcumin as a discoloring component, wherein said discoloring component is supported on granular activated alumina, into contact with a gas to be detected that may contain a halogen compound, as said detector agent is disposed in a position where it can be visually observed.

4. A method for detecting at least one halogen compound, which comprises visually observing a detector agent for detecting a halogen compound, which comprises curcumin as a discoloring component, wherein said discoloring component is supported on granular activated alumina, wherein the detector agent is disposed on an upper layer of a solid treatment agent for removing or decomposing a halogen compound, as a gas to be treated is caused to flow from a bottom side of a container containing said solid treatment agent, whereby a halogen compound is detected to judge the deterioration of said solid treatment agent.

5. The method of claim 3, wherein the halogen compound to be detected is selected from the group consisting of $SiH_2Cl_2$, HF, $F_2$, HBr, $Cl_2$, $ClF_3$, $TiCl_4$, $BCl_3$, HI and mixtures thereof.

6. The method of claim 4, wherein the halogen compound to be detected is selected from the group consisting of $SiH_2Cl_2$, HF, $F_2$, HBr, $Cl_2$, $ClF_3$, $TiCl_4$, $BCl_3$, HI and mixtures thereof.

* * * * *